United States Patent [19]

Allen

[11] 4,279,886

[45] Jul. 21, 1981

[54] TEST FOR PANCREATIC EXOCRINE FUNCTION

[75] Inventor: Robert H. Allen, Englewood, Colo.

[73] Assignee: University Patents, Inc., Norwalk, Conn.

[21] Appl. No.: 270

[22] Filed: Jan. 2, 1979

[51] Int. Cl.$^3$ .................... A61K 49/00; A61K 43/00; G01T 1/00
[52] U.S. Cl. ...................................... 424/1; 128/659; 424/1.5; 424/9
[58] Field of Search ................. 424/1, 9, 1.5; 128/659

[56] References Cited

U.S. PATENT DOCUMENTS

| | | | |
|---|---|---|---|
| 3,786,140 | 1/1974 | Meyer-Bertenrath et al. | 424/9 |
| 3,903,253 | 9/1975 | Rolland | 424/9 |
| 4,133,951 | 1/1979 | Charlton et al. | 424/1.5 |

OTHER PUBLICATIONS

Brugge et al., Gastroenterology, 78(1980), 937–949.
Allen et al., Gastroenterology, 75(1978), 761–762.
von der Lippe et al., Scand. J. Gastroenterol., 12(1977), 183–187.
Allen et al., J. Clin. Inv., 61(1978) 47–54, 1628–1634.
von der Lippe et al., Chem. Abstracts, vol. 88, No. 1, Jan. 1978, Abstract No. 451q.

Primary Examiner—Benjamin R. Padgett
Assistant Examiner—Christine M. Nucker
Attorney, Agent, or Firm—Donald W. Margolis; H. Kenneth Johnston, II

[57] ABSTRACT

It has been determined that ingested vitamin $B_{12}$ is bound by R protein in gastric juice, but that it is not capable of absorption in this form. In a system with a normally functioning exocrine pancreas, R protein is degraded by pancreatic proteases in the small intestine, which then allows the $B_{12}$ to be transferred and bound to intrinsic factor protein (IF) from which it can be absorbed. This phenomenon serves as the basis for a test for pancreatic exocrine function in which the following compositions are ingested: (1) a complex of IF and $B_{12}$ in which the $B_{12}$ is labelled; (2) a combination of another binding material, such as R protein, and $B_{12}$, in which the $B_{12}$ is labelled (in preferred embodiments the $B_{12}$ is labelled differently than the $B_{12}$ in the IF-$B_{12}$ complex); and (3) means for preventing R protein in the gastric juices from removing $B_{12}$ from the IF-$B_{12}$ complex, (in preferred embodiments such means are $B_{12}$ analogues that bind to R protein in the gastric juices; but which do not bind to IF).

46 Claims, No Drawings

TEST FOR PANCREATIC EXOCRINE FUNCTION

The invention described herein was made, in part, in the course work under grant or award from the Department of Health, Education and Welfare.

BACKGROUND OF THE INVENTION

1. Field of the Invention

The present invention relates to methods and compositions for testing pancreatic exocrine function. More specifically, it relates to the use of the vitamin $B_{12}$ ingestion system as a means of measuring pancreatic exocrine function.

2. Prior Art

The human pancreas contains endocrine portions and an exocrine portion. The endocrine portions actually consist of a multitude of small islets that synthesize and release hormones into the blood. The exocrine portion carries the endocrine islets and makes up the bulk of the pancreas. When functioning properly, the exocrine portion synthesizes a number of digestive enzymes such as amylase, trypsin, chymotrypsin, elastase, lipase, and others. These enzymes are released into the upper part of the small intestine and are essential for proper digestion and nourishment.

On occasion the exocrine portion of the pancreas may be caused to malfunction. Such malfunction may be due to damage caused in a variety of ways, including chronic alcoholism, trauma, and pancreatic cancer. Due to the fact that the pancreas is located deep in the abdomen it is extremely difficult to evaluate clinically. X-rays and scans of the pancreas are discernably abnormal in only a relatively small proportion of patients with actual pancreatic exocrine insufficiency.

Several tests of pancreatic exocrine function are currently available. However, such tests are time consuming, cumbersome and inconvenient. One prior art test involves measuring the amount of fat in feces. This fecal fat test is based on the fact that fecal fat is increased in the absence of the pancreatic exocrine enzyme lipase which is required for the digestion and absorption of fat in the intestine. To accomplish this test the patient must save all of his feces for 72 hours and the feces must then be analyzed for fat in the laboratory. This test is unpleasant for the patient and for laboratory personnel and, even then, it is not available at many hospitals. Furthermore, this fecal fat test lacks specificity to pancreatic exocrine insufficiency, since it also provides abnormal results in a variety of intestinal diseases such as Crohn's disease and sprue.

Another prior art test, duodenal intubation, involves placing a tube into the upper small intestine via the mouth and stomach and then collecting pancreatic juice which is subsequently analyzed for volume, bicarbonate and pancreatic enzymes. This test is time consuming, expensive, inconvenient and unpleasant for the patient, and again, it is available at only a relatively small number of medical centers. It is therefore seen that there is presently no convenient easily applied test for pancreatic exocrine function.

It has been noted, for example, employing standard Schilling tests that $B_{12}$ is malabsorbed by about 50% of patients diagnosed to have pancreatic exocrine insufficiency. However, $B_{12}$ malabsorbtion by itself is not a reliable indication of pancreatic exocrine dysfunction as $B_{12}$ absorption is not abnormal in more than about one-half of patients with such disfunction, and further, as $B_{12}$ absorption is also abnormal in cases of pernicious anemia and also as a result of a number of intestinal diseases.

The Schilling test, noted above, utilizes labelled $B_{12}$, for example, $B_{12}$ including a radioactive cobalt isotope, to measure and evaluate absorption of $B_{12}$ by the digestive system. A modified or dual labelling Schilling test is commercially available, which uses two differently labelled forms of $B_{12}$, one of which is bound to intrinsic factor, and the other of which is unbound. However, such tests utilizing labelled $B_{12}$ have at no time been used to independently evaluate pancreatic exocrine function.

For many years it was believed that ingested vitamin $B_{12}$ was bound in the form of a complex to a protein known as intrinsic factor (IF) present in the gastric juices of the stomach. It was further believed that this IF-$B_{12}$ complex remained intact until it attached to specific receptors located at the end of the small intestine at which receptors the $B_{12}$ was unbound and absorbed into the body. It has now been determined that this model for $B_{12}$ ingestion is incorrect and that use of the correct $B_{12}$ ingestion model can now serve as the basis of accurately evaluating pancreatic exocrine function.

BRIEF DESCRIPTION OF THE INVENTION

As used throughout this application, the term "$B_{12}$" shall mean and include "vitamin $B_{12}$" and the various "cobalamin" compounds and "corrinoids" which are forms of or antecedents of vitamin $B_{12}$.

The present invention is based on a recently discovered model of $B_{12}$ absorption into the system. As already noted, it had been previously believed that ingested $B_{12}$ formed a complex with and was bound to the protein designated as "intrinsic factor" (IF) which is normally present in the gastric juices. It has now been determined that the mechanism for $B_{12}$ absorption is a two-step process. In this two-step process $B_{12}$ initially binds preferentially with another protein, designated as "R protein," which is also normally present in the gastric juices. This complexing of $B_{12}$ with R protein is overwhelming, even in the presence of IF protein. On the order of about 98 to 99% of the $B_{12}$ reacts with normally available R protein to form a complex, which is herein designated as "R-$B_{12}$." In situations in which $B_{12}$ is already complexed with IF, available R protein will remove the $B_{12}$ from the IF to overwhelmingly form R-$B_{12}$. After R-$B_{12}$ complex enters the small intestine it is then degraded by enzymes from the exocrine pancreas, such as trypsin, chymotrypsin and elastase. Following this degradation the $B_{12}$ can then bind with IF to form an IF-$B_{12}$ complex from which $B_{12}$ is eventually ingested via receptors at the end of the small intestine.

It has also been recently discovered that there are vitamin $B_{12}$ analogues, which respond to many tests in a manner similar to $B_{12}$, but which do not support the same bodily functions as $B_{12}$. The relationship between $B_{12}$ and analogue $B_{12}$, as well as the accurate testing of $B_{12}$ in the presence of $B_{12}$ analogue is set forth in great detail in pending U.S. patent application Ser. No. 893,524, also by Robert H. Allen and assigned to the same assignee as the present application. It has also been discovered that while R protein will complex with either $B_{12}$ or analogue $B_{12}$, that IF is specific to and will only bind with true $B_{12}$.

Discovery of the two-step $B_{12}$ ingestion process, of $B_{12}$ analogue, and of the ability of $B_{12}$ analogue to bind with R protein, but not with IF, serve as the basis for the present invention.

It is postulated that since $B_{12}$ initially preferentially binds with R protein in the digestive system to form R-$B_{12}$ complex, and that since the R-$B_{12}$ complex is stable, until acted upon by enzymes produced by the exocrine portion of the pancreas, that a method of accurately determining the ingestion of initially $B_{12}$ bound to R reflects on the availability of digestive enzymes from the exocrine portion of the pancreas. It is further postulated that the availability of digestive enzymes from the exocrine portion of the pancreas reflects on the functioning of the exocrine portion of the pancreas.

This theory is made the basis of the test of the present invention, which, by providing two differently labelled $B_{12}$ compounds and manipulating the digestive environment of the patient undergoing evaluation provides a test for pancreatic exocrine function. While the present invention may simplistically be considered a "dual labelled" Schilling type test, it requires steps and materials not normally used in a Schilling test.

For purposes of this specification a first labelled $B_{12}$ compound designated as "$B^*_{12}$" and a second, but differently labelled $B_{12}$ compound, designated as "$B^{**}_{12}$" are required. $B^*_{12}$ and $B^{**}_{12}$ may be, for example, radioactive ($^{57}$Co) $B_{12}$ and radioactive ($^{58}$Co) $B_{12}$. Other isotopes or means of labelling $B_{12}$, may also be used.

In the practice of the present invention, as a test for exocrine pancreatic function, a patient ingests, either as a single mixed composition or as a series of several compositions: (1) vitamin $B^{}_{12}$ bound to intrinsic factor, and hereinafter designated as "IF-$B^{}_{12}$;" (2) vitamin $B^*_{12}$ bound to R protein, and hereinafter referred to as "R-$B^*_{12}$;" and (3) a substantial amount of $B_{12}$ analogue. In preferred embodiments a fourth component containing unbound intrinsic factor, hereinafter "IF," is also included.

Subsequently, as detailed below, the amount and ratio of $B^*_{12}$ and $B^{**}_{12}$ absorbed, as assayed by measuring the amounts in the urine using the Schilling procedure is indicative of the function of the exocrine pancreas.

In the general practice of the process of the present invention the patient undergoing test is given an injection of $B_{12}$, or is otherwise treated to remove free binding protein from his blood, and caused to ingest IF-$B^{**}_{12}$, R-$B^*_{12}$ and $B_{12}$ analogue. Subsequently his urine is collected and the amount and ratio of $B^*_{12}$ and $B^{**}_{12}$ measured. Normal exocrine pancreas function will be attributed to patients who excrete $B^*_{12}$ and $B^{}_{12}$ in substantially the same proportion as it was ingested. Abnormal pancreatic exocrine function will be attributed to patients who excrete substantially more $B^{}_{12}$ than $B^*_{12}$ in relation to the proportions ingested.

The following mechanism is postulated for this test. The vitamin $B_{12}$ injection which the patient is given binds the subject's then available binding proteins in the blood and serum so that that binding material is not available to bind with the ingested $B^*_{12}$ and $B^{}_{12}$ samples, both of which can thus be excreted in the urine in substantial amounts. In the digestive system the ingested $B_{12}$ analogue binds with substantially all of the R protein naturally in the stomach, thus making the natural R protein substantially unavailable for competition with the IF-$B^{}_{12}$ so that the IF is not replaced with R in the stomach to form R-$B^{**}_{12}$.

In evaluating the results of the test of the present invention, subjects with normal pancreatic exocrine function are found to absorb and excrete significant amounts of both $B^*_{12}$ and $B^{**}_{12}$ in about the same proportion as the amounts of $B^*_{12}$ and $B^{}_{12}$ originally ingested. This is due to the fact that the IF-$B^{}_{12}$ is readily available for absorption without interference from R protein (which has been bound by the ingested $B_{12}$ analogue), while the pancreatic exocrine enzymes in the normal system cause the R-$B^*_{12}$ to be degraded so that the $B^*_{12}$ can then bind with IF in the system for absorption via the receptors. However, not much of either the $B^*_{12}$ or $B^{**}_{12}$ remains in the body, since the normal binding protein has been bound by a vitamin $B_{12}$ injection.

Utilizing the test of the present invention, patients with pancreatic exocrine insufficiency will absorb and excrete substantial amounts of $B^{**}_{12}$ which was initially bound with IF. However, using this test, they will absorb and excrete very little $B^*_{12}$. This is due to the fact that, as ingested the $B^*_{12}$ was initially bound to R protein. Therefore, the absence or insufficiency of pancreatic exocrine enzymes to digest the R-$B^*_{12}$ does not allow the $B^*_{12}$ to be released from R protein for binding with IF and for absorption as IF-$B^*_{12}$. Thus, during the practice of the present invention, low excretion of $B^*_{12}$ signals a lack of pancreatic exocrine enzyme in the system, and thus a malfunctioning exocrine pancreas.

In the absence of pancreatic disease, patients having intestinal diseases, which interfere with $B_{12}$ absorption, absorb and excrete decreased, but essentially proportional amounts of $B^*_{12}$ and $B^{**}_{12}$ to the amounts ingested.

Patients with both pancreatic exocrine disease and intestinal disease will also absorb and excrete decreased amounts of both $B^*_{12}$ and $B^{**}_{12}$, but the amount of decrease for the $B^*_{12}$ is disproportionately greater than the amount of decrease for the $B^{**}_{12}$.

In preferred embodiments, the patient undergoing test is also caused to ingest unbound IF. This assures the availability of IF to bind with $B^*_{12}$ when and if it becomes available from degraded R-$B^*_{12}$. This assures the test against erroneous results should the patient fail to have sufficient IF in his gastric juices.

Other embodiments of the present invention include mixtures of compositions containing IF-$B^{**}_{12}$, R-$B^*_{12}$ and $B_{12}$ analogue, with and without unbound IF. Methods of making IF-$B^{**}_{12}$ and the R-$B^*_{12}$ complex constitute yet other embodiments of the present invention.

The foregoing and other objects, features and advantages of the invention will be apparent from the following more particular description of preferred embodiments of the invention.

DETAILED DESCRIPTION OF THE INVENTION

The following is set forth as a prelude to describing the process and compositions of the present invention. They provide details of certain experiments which were carried on and which led to the hypothesis upon which the present invention is based. Additionally, they provide evaluation of that hypothesis and further indicate the degree of specificity and sensitivity of the tests of the present invention.

As already noted, the present invention is based upon a $B_{12}$ absorption model which proposes that ingested $B_{12}$ is first bound to R in the gastric juices. It is further proposed that only after pancreatic proteases act is the R-$B_{12}$ complex degraded so that $B_{12}$ can bind with IF for absorption into the system. Based on this model normal subjects should absorb $B_{12}$ originating as intrinsic factor-$B_{12}$ and $B_{12}$ originating as R protein-$B_{12}$ in equivalent amounts. Furthermore, ratios of excreted $B_{12}$ originating as intrinsic factor-$B_{12}$ to $B_{12}$ originating as R protein-$B_{12}$ should be close to the ratio at which they were ingested. Subjects with pancreatic exocrine insufficiency should absorb $B_{12}$ originating as intrinsic factor-$B_{12}$ normally, but should malabsorb $B_{12}$ originating as R protein-$B_{12}$. Thus, if given substantially equal amounts of IF-$B_{12}$ and R-$B_{12}$ they should have high ratios for $B_{12}$ originating as intrinsic factor-$B_{12}$ to R protein-$B_{12}$. Subjects with intestinal disease would often malabsorb $B_{12}$ originating as both intrinsic factor-$B_{12}$ and R protein-$B_{12}$, but such malabsorption should be equivalent.

As used herein, "$B_{12}^{12}$" shall always designate $B_{12}$ originating as an intrinsic factor-$B_{12}$ complex, and "IF-$B_{12}^{12}$" shall designate that complex. "$B_{12}^{r}$" shall always designate $B_{12}$ originating as R protein-$B_{12}$ complex, and "R-$B_{12}^{r}$" shall designate the latter complex.

MATERIALS AND METHODS ($^{57}$Co)$B_{12}$ (12.5 uCi/nmol) and ($^{58}$Co)$B_{12}$ (4.0 uCi/nmol) were obtained from Amersham-Searle Corp., Arlington Heights, Ill. The ($^{58}$Co)$B_{12}$ was obtained in the form of capsules such as those utilized in the Dicopac Schilling Test Kit. Each capsule was opened and the contents dissolved in 5.0 ml of 0.15 M NaCl solution and centrifuged at 10,000× gravity for 15 minutes at a temperature of 4° C. Then the supernatant liquid containing the ($^{58}$Co)$B_{12}$ was stored at −20° C. Crystalline $B_{12}$ was obtained from Sigma Chemical Company, St. Louis, Mo., as CN-cobalamin assayed spectrophotometrically, and utilized to dilute the ($^{57}$Co)$B_{12}$ to a specific activity of 2.5 uCi/nmol.

$B_{12}$ analogue in the form of cobinamide was prepared and isolated as described by Allen et al J. Clin. Invest. 60:1381–1392, 1977, except that cobinamide and 13-epicobinamide were not separated from each other by paper chromatography.

Crystalline hog trypsin and bovine chymotrypsin were obtained from Sigma Chemical Company.

Crystalline hog elastase was obtained from P-L Biochemicals, Inc., Milwaukee, Wis.

Pancreatic extract was obtained from Kremers-Urban Company, Milwaukee, Wis., in the form of capsules designated as (KU-ZYME HP).

Homogenous human intrinsic factor, hog R protein, rabbit anti-human intrinsic factor serum, and human anti-intrinsic factor blocking antibodies were obtained as described previously by Katz et al, J. Clin. Invest. 53:1274–1283, 1974.

Human saliva served as the source of human R protein.

Human duodenal juice was collected with a dual lumen duodenal tube. The distal opening was positioned at the ligament of Trietz under fluoroscopic control with the second opening being located 12 cm proximally. Pancreatic secretion was stimulated by perfusing a mixture of essential amino acids and glucose through the proximal opening at a rate of 6 ml/min and samples were collected through the distal opening. The perfusate used to stimulate pancreatic secretion contained the following, in g/liter: lysine, 5.5; tryptophan, 2.0; phenylalanine, 5.5; methionine, 8.5; threonine, 3.8; leucine, 7.9; isoleucine, 3.7; valine, 6.1; and glucose, 50.

Vitamin $B_{12}$ binding assays were performed as described by Allen et al, J. Biol. Chem. 248: 3660–3669 (1973).

The transfer of ($^{57}$Co)$B_{12}$ from R protein to intrinsic factor was performed at pH 8.0 and was based on the precipitation of ($^{57}$Co)$B_{12}$ intrinsic factor with rabbit-anti-intrinsic factor antisera in 40% $(NH_4)_2SO_4$ as described by Allen et al, J. Clin. Invest. 61: 47–54, 1978.

Trypsin was assayed, as described by Erlanger et al, Arch, Biochem. Biophy. 95: 271–278, 1961, with benzoyl arginine p-nitroanilide, and the results were expressed as ug equivalents of hog trypsin which was used as the standard.

The following studies are indicative of the fact that pancreatic enzymes are required in order to transfer $B_{12}$ from $B_{12}$-R complexes to $B_{12}$-IF complexes.

The results of in vitro studies with human R protein and purified pancreatic proteases are presented in Table 1 and indicate that 50% of the $B_{12}^{r}$ was transferred from human R protein to human intrinsic factor at concentrations of hog trypsin and bovine chymotrypsin of 80 and 1200 ug/ml, respectively. Hog elastase was the least effective in transferring $B_{12}^{r}$ from R protein to IF, with only 11% transfer occurring at a hog elastase enzyme concentration of 2250 ug/ml. However, these proteases appear to act synergistically since an equal mixture of all 3 enzymes effected 50% transfer at a total protein concentration of 63 ug/ml (concentration of each enzyme 21 ug/ml).

The results of identical studies performed simultaneously with hog R protein are also shown in Table 1. At enzyme concentrations of 2250 ug/ml only 11, 4 and 0% of $B_{12}^{r}$ was transferred from hog R protein to human intrinsic factor with hog trypsin, bovine chymotrypsin, and hog elastase, respectively. Only 6% transfer of $B_{12}^{r}$ occurred with an equal mixture of all 3 enzymes at a total enzyme concentration of 2250 ug/ml. These results indicate that hog R protein-$B_{12}^{r}$ is 50–100 fold more resistant to the action of pancreatic proteases than is human R protein-$B_{12}^{r}$.

TABLE 1

ABILITY OF PURIFIED PANCREATIC ENZYMES TO EFFECT THE TRANSFER OF ($^{57}$Co)$B_{12}$ FROM R PROTEIN TO INTRINSIC FACTOR

| enzyme added (ug/ml) | Percent Transfer of ($^{57}$Co)$B_{12}$ from Human R Protein to Human Intrinsic Factor by Various Pancreatic Enzymes | | | |
|---|---|---|---|---|
| | trypsin (%) | chymotrypsin (%) | elastase (%) | all three (%) |
| 0 | 0 | 0 | 0 | 0 |
| 5.5 | 5 | 0 | 0 | 5.7 |
| 16.5 | 15 | 0 | 0 | 19 |
| 55 | 39 | 0 | 0 | 46 |
| 170 | 72 | 4 | 0.3 | 82 |
| 550 | 91 | 30 | 5 | 96 |
| 2250 | 94 | 70 | 11 | 97 |

| enzyme added (ug/ml) | Percent Transfer of ($^{57}$Co)$B_{12}$ from Hog R Protein to Human Intrinsic Factor by Various Pancreatic Enzymes | | | |
|---|---|---|---|---|
| | trypsin (%) | chymotrypsin (%) | elastase (%) | all three (%) |
| 0 | 0 | 0 | 0 | 0 |
| 5.5 | 0 | 0 | 0 | 0 |
| 16.5 | 0 | 0 | 0 | 0 |
| 55 | 0 | 0 | 0 | 0 |
| 170 | 0 | 0 | 0 | 0 |
| 550 | 1.4 | 0.7 | 0 | 1 |

TABLE 1-continued
ABILITY OF PURIFIED PANCREATIC ENZYMES TO EFFECT THE TRANSFER OF $(^{57}Co)B_{12}$ FROM R PROTEIN TO INTRINSIC FACTOR

| | | | | |
|---|---|---|---|---|
| 2250 | 13 | 4 | 0 | 5.5 |

Assays were performed in a volume of 0.45 ml of 0.013 M Tris (Hydroxymethyl) Aminomethane-HCl pH 8.0, 0.187 M NaCl, containing enzyme as indicated, 26.67ug of bovine serum albumin, and 1 pmol of $(^{57}Co)B_{12}$ prebound to 1 pmol of R protein. After incubating for 30 minutes at 37° C., 1.5 pmol of Human Intrinsic Factor was added in 0.05 ml and the reaction was incubated for another 30 minutes at 37° C. The samples were then cooled in ice water for 5 minutes and 0.1 ml of rabbit Anti Human Intrinsic Factor anti-serum was added. After an additional 30 minutes, 0.5 ml of $H_2O$ saturated with $(NH_4)_2SO_4$ was added, followed by centrifugation at 20,000 × g at 4° C. for 30 minutes. A portion, 0.5 ml, of the supernatant was then assayed for $(^{57}Co)B_{12}$. This reflected the amount of $(^{57}Co)B_{12}$ still bound to R since any $(^{57}Co)B_{12}$ transferred to Intrinsic Factor was precipitated under the assay conditions.

TABLE 2
ABILITY OF CRUDE PANCREATIC ENZYMES TO EFFECT THE TRANSFER OF $(^{57}Co)B_{12}$ FROM R PROTEIN TO INTRINSIC FACTOR

| | Percent Transfer of $(^{57}Co)B_{12}$ from Human R Protein to Human Intrinsic Factor | | |
|---|---|---|---|
| solution present# | Hog pancreatic | Human duodenal juice | |
| (% of full strength) | extract | unstimulated | stimulated |
| 0 | 0 | 0 | 0 |
| 0.155 | | 0 | 2 |
| 0.225 | 0 | | |
| 0.335 | | 0.5 | 9 |
| 0.66 | 16 | 4 | 32 |
| 2.20 | 61 | | |
| 2.75 | | 15 | 90 |
| 5.50 | | 52 | 94 |
| 6.60 | 89 | | |
| 11.0 | | 83 | 97 |
| 22.0 | 93 | | |
| 43.5 | | 96 | 99 |
| 50.0 | 98 | | |
| 66.0 | | 98 | 99 |
| 86.0 | 99 | 99 | 100 |

| | Percent Transfer of $(^{57}Co)B_{12}$ from Hog R Protein to Human Intrinsic Factor | | |
|---|---|---|---|
| solution present# | Hog pancreatic | Human duodenal juice | |
| (% of full strength) | extract | unstimulated | stimulated |
| 0 | 0 | 0 | 0 |
| 0.225 | 0 | | |
| 0.66 | 0 | | |
| 1.30 | | 0 | 0 |
| 2.20 | 0.3 | | |
| 5.5 | | 0 | 3.3 |
| 6.60 | 1.7 | | |
| 11.0 | | 0 | 8.7 |
| 22.0 | 9 | 0 | 16 |
| 33.0 | | | 22 |
| 44.0 | | 3.7 | 30 |
| 51.0 | 24 | | |
| 66.0 | | 10 | 40 |
| 87.0 | | 13 | 45 |
| 90.0 | 39 | | |

Assay were performed as described in Table 1.
% of full strength = (amount of sample assayed ÷ initial incubation volume) × 100% For example, if 0.2 ml of Human Duodenal Juice was added to this assay the "% of full strength" would equal
$$\frac{0.2 \text{ ml}}{0.45 \text{ ml}} \times 100\% = 44.4\%$$
All volume differences associated with the various amounts of solution present were corrected with 0.15 M NaCl.

Table 2 shows the results of similar studies performed with a freshly prepared solution of hog pancreatic extract (KU-ZYME HP) and freshly collected samples of human duodenal juice obtained before and after pancreatic secretion was stimulated by the duodenal perfusion of essential amino acids. As shown in Table 2, all three solutions caused 50% transfer of $B_{12}$ from human R protein to human intrinsic factor when they were present at 1 to 5% of their full strength. The sample of human duodenal juice obtained after pancreatic stimulation was approximately 5 times more potent than the unstimulated sample, while the solution of hog pancreatic extract was intermediate in this regard. The three solutions had the same relative potencies when tested with hog R protein-$B\overset{*}{\uparrow}_2$ (Table 2), but only about 13-46% of the $B\overset{*}{\uparrow}_2$ was transferred to human intrinsic factor when they were tested at 89% of their full strength. These studies support the concept that hog R protein-$B\overset{*}{\uparrow}_2$ is more resistant to the action of pancreatic enzymes than is human R protein-$B\overset{*}{\uparrow}_2$.

Table 3 shows the results of an experiment in which multiple serial samples of duodenal juice were collected from a normal subject before and after pancreatic secretion was stimulated by the duodenal perfusion of essential amino acids. Trypsin activity and the ability to transfer $B_{12}$ from R protein to intrinsic factor increased in parallel after pancreatic stimulation. This provides additional evidence for the concept that the transfer of $B_{12}$ from R protein to intrinsic factor is a specific function of pancreatic enzymes.

TABLE 3
CORRELATION OF TRYPSIN ACTIVITY AND THE ABILITY TO TRANSFER $(^{57}Co)B_{12}$FROM R PROTEIN TO IF IN HUMAN DUODENAL JUICE BEFORE AND AFTER PANCREATIC STIMULATION

| Time after pancreatic stimulation (minutes) | Trypsin+ ug/ml | Percent transfer of $(^{57}Co)B_{12}$ from R protein to Human Intrinsic Factor++ | |
|---|---|---|---|
| | | Human R (%) | Hog R (%) |
| −10 | 37 | 7 | 0 |
| −5 | 54 | 11 | 0 |
| 0 | 35 | 1.4 | 0 |
| +5 | 97 | 19 | 0 |
| +10 | 272 | 82 | 10 |
| +15 | 360 | 89 | 14 |
| +20 | 271 | 83 | 9 |
| +25 | 189 | 76 | 1.7 |
| +30 | 129 | 60 | 0 |
| +35 | 138 | 54 | 0 |
| +40 | 145 | 52 | 0 |
| +45 | 145 | 57 | 0 |
| +50 | 123 | 38 | 0 |
| +55 | 172 | 58 | 0 |
| +60 | 132 | 41 | 0 |
| +65 | 135 | 46 | 0 |
| +70 | 166 | 50 | 0 |
| +75 | 120 | 42 | 0 |
| +80 | 95 | 30 | 0 |
| +85 | 111 | 32 | 0 |

+Assayed as described in specifications
++Assayed as described in Table 1; 0.020 ml and 0.400 ml of each sample were used for the human R and hog R assays, respectively.

It has been found that dog R protein is similar to hog R protein, when it is used in place of hog R protein in experiments similar to those in Tables 1, 2 and 3. It has also been found that rat IF and hog IF are similar to human IF when used in the practice of the present invention.

In the preferred process of the present invention, the subject to be tested has a digestive tract substantially free of undigested food or unprocessed waste materials. This is accomplished, for example, by fasting the subject for about 8 to 12 hours. Then the subject is caused to orally ingest the following, either separately or in combination:

(1) One labelled form of $B\overset{*}{\uparrow}_2$ bound to intrinsic factor ($B\overset{*}{\uparrow}_2$-IF);
(2) A second labelled form of $B_{12}$ bound to R protein ($B\overset{*}{\uparrow}_2$-R);
(3) An unlabelled $B_{12}$ analogue that binds only to R protein; and (4) Free intrinsic factor (IF) (optional).

These test solutions were prepared by combining 1 ml of H$_2$O containing 0.2 nmol of ($^{57}$Co)B$_{12}$ (2.5 uCi/nmol) with 0.6 nmol of purified human intrinsic factor present in 4.0 ml of 0.01 M potassium phosphate, pH 7.5, containing 0.15 M NaCl and 50 ug/ml of bovine serum albumin. Alternatively, human gastric juice which contains both IF and R protein could be utilized after incubation with suitable B$_{12}$ analogue, such as cobinamide, B$_{12}$ (bde-OH) or (3,5,6-Me$_3$ benzimidazole) B$_{12}$ in 1 to 1,000,000 fold excess with respect to R protein. These B$_{12}$ analogues bind to R, but not IF. Thus when ($^{57}$Co)B$_{12}$ is subsequently added it is bound only by IF since all of the R is already bound. In a separate tube, 5.0 ml of 0.15 M NaCl containing 0.2 nmol of ($^{58}$Co)B$_{12}$ (4.0 uCi/nmol) was combined with 0.3 nmol of R protein present in 5.0 ml of 0.01 M potassium phosphate, pH 7.5, containing 0.15 M NaCl and 50 ug/ml of bovine serum albumin. The IF and R protein solutions were incubated at room temperature for 30 minutes and then cooled to 4° C. Cobinamide, 200 nmol in 1.0 ml of 0.15 M NaCl, was added to the R protein solution and after incubating for 30 minutes at 4° C. the intrinsic factor and R protein solutions were combined and stored at −20° C. After thawing, it was found that greater than 95% of the ($^{57}$Co)B$_{12}$ and ($^{58}$Co)B$_{12}$ were still bound by IF and R protein, respectively, based on assays employing charcoal adsorption and precipitation with specific antisera.

Test solutions were administered orally to subjects who had been fasted for about 8 to 12 hours. An intramuscular injection of 1 mg of nonradioactive (unlabelled) B$_{12}$ was given at substantially the same time as the oral test solution. Subsequently, about two hours after the test was begun, the subject was allowed to end his fast. The subject's excreted urine was then collected for 24 hours after the administration of the test solution and was assayed for ($^{57}$Co) and ($^{58}$Co) with a Beckman Gamma 300 System, Beckman Instruments, Inc., Fullerton, Calif.

In one preferred embodiment the effect of pancreatic exocrine function on the ability to absorb B$_{12}$ bound to human R protein or hog R protein, versus that of B$_{12}$ bound to human intrinsic factor, was tested by performing a series of dual label Schilling type tests. Each orally administered test sample contained 0.2 nmol of ($^{58}$Co)B$_{12}$ bound to either human R protein or hog R protein, 0.2 nmol of ($^{57}$Co)B$_{12}$ bound to human IF, 0.4 nmol of human IF and 200 nmol of nonradioactive cobinamide, a B$_{12}$ analogue. Cobinamide B$_{12}$ analogue binds to R protein but does not bind with IF. When ingested it serves to prevent endogenous R protein, normally present in the gastric juices, from removing the ($^{57}$Co)B$_{12}$ from human IF within the gastrointestinal tract. Nonradioactive B$_{12}$, 1 mg, was injected intramuscularly in conjunction with the oral ingestion of the test solutions. This injection served to saturate B$_{12}$-binding proteins in the plasma, thus allowing substantial urinary excretion of absorbed ($^{57}$Co)B$_{12}$ and ($^{58}$Co)B$_{12}$ which could then be measured in 24 hour urine collections.

TABLE 4

Comparison of the absorption of ($^{58}$Co)B$_{12}$* bound to Human and Hog R protein (R), versus that of ($^{57}$Co)B$_{12}$** bound to Human intrinsic factor (IF) in dual label pancreatic tests performed on a patient with pancreatic exocrine insufficiency.*

| | | Percentage of administered B$_{12}$ excreted in urine | | |
|---|---|---|---|---|
| R protein | Addition+ | IF-B$_{12}$** (%) | R-B$_{12}$* (%) | IF-B$_{12}$**/R-B$_{12}$* |
| Human | None | 19.1 | 1.5 | 12.7 |
| Hog | None | 23.6 | 0.6 | 39.3 |
| Human | Trypsin++ | 25.8 | 19.9 | 1.3 |
| Hog | Trypsin++ | 16.0 | 1.8 | 8.9 |
| Hog | Hog pancreatic extract# | 14.3 | 6.3 | 2.2 |

*Orally administered solutions (see Methods) contained 0.2 nmol of ($^{58}$Co)B$_{12}$* bound to Human or Hog R protein, 0.2 nmol of ($^{57}$Co)B$_{12}$** bound to Human IF, enough free IF to bind 0.4 nmol of B$_{12}$, and 200 nmol of nonradioactive cobinamide. The patient was No. 13 per Table 5.
+Given orally immediately following the solution containing labelled B$_{12}$.
++Crystalline Hog trypsin, 50 mg, freshley dissolved in 50 ml of 0.001M HCl.
Four pancrelipase capsules (KU-ZYME HP).

The results of these tests when performed on a subject with known pancreatic exocrine insufficiency are shown in Table 4 and are consistent with the in vitro experiments in the following ways: (1) B$_{12}$ originating as human R protein-B$_{12}$ and hog R protein-B$_{12}$ were absorbed less than 10% as well as B$_{12}$ originating as human IF-B$_{12}$; (2) B$_{12}$ originating as hog R protein-B$_{12}$ was absorbed less well than B$_{12}$ originating as human R protein-B$_{12}$; (3) hog trypsin corrected the malabsorption of B$_{12}$ originating as human R protein-B$_{12}$ to a much greater extent than it corrected the malabsorption of B$_{12}$ originating as hog R protein-B$_{12}$; and (4) hog pancreatic extract was more potent than hog trypsin in correcting the malabsorption of B$_{12}$ originating as hog R protein-B$_{12}$. Because of its greater availability and resistance to pancreatic enzymes, hot R protein was utilized for the remainder of the preferred embodiments presented below.

Following are details of how the relative absorption of B$_{12}$ originating as human IF-B$_{12}$ and B$_{12}$ originating as hog R protein-B$_{12}$, serves as a diagnostic test for pancreatic exocrine insufficiency. The results of dual label Schilling type tests employing human IF-B$_{12}$ and hog R protein-B$_{12}$ performed on normal subjects, and patients with pancreatic and other diseases are shown in Table 5. In 11 normal subjects the percent of orally administered B$_{12}$ in 24-hour urine samples ranged from about 15.4% to 26.7% (mean 21.9%) for B$_{12}$ originating as IF-B$_{12}$ and from about 10.0% to 23.1% (mean 17.3%) B$_{12}$ for B$_{12}$ originating as hog R protein-B$_{12}$. The ratio of urine excreted B$_{12}$ to B$_{12}$ ranged from about 1.0 to 1.8 (mean 1.3). The fact that normal subjects usually absorbed slightly more B$_{12}$ originating as IF-B$_{12}$ than B$_{12}$ originating as hog R protein-B$_{12}$ is consistent with the above in vitro observation, that human pancreatic juice is somewhat limited in its ability to effect the transfer of B$_{12}$ from hog R protein to human IF.

TABLE 5

Results of dual label pancreatic tests performed on normals, and patients with pancreatic and other gastrointestinal diseases#

| Subject # | Age Yr | Sex | Fecal Fat+ (g/24 Hr) | Disease | IF-$B_{12}$** (%) | R-$B_{12}$* (%) | IF-$B_{12}$**/ R-$B_{12}$* |
|---|---|---|---|---|---|---|---|
| Normal subjects | | | | | | | |
| 1 | 53 | F | | None | 24.9 | 13.8 | 1.8 |
| 2 | 24 | F | | " | 16.4 | 10.0 | 1.6 |
| 3 | 28 | F | | " | 26.7 | 19.3 | 1.4 |
| 4 | 35 | M | | " | 21.0 | 16.8 | 1.3 |
| 5 | 62 | M | | " | 15.4 | 12.1 | 1.3 |
| 6 | 34 | F | | " | 25.6 | 20.1 | 1.3 |
| 7 | 31 | M | | " | 23.2 | 19.8 | 1.2 |
| 8 | 29 | M | | " | 18.9 | 16.4 | 1.2 |
| 9 | 26 | F | | " | 23.0 | 18.8 | 1.2 |
| 10 | 32 | M | | " | 22.9 | 20.5 | 1.1 |
| 11 | 40 | M | | " | 23.1 | 23.1 | 1.0 |
| | | | | mean | (21.9) | (17.3) | (1.3) |
| | | | | range | (15.4–26.7) | (10.0–23.1) | (1.0–1.8) |
| | | | | mean ± 2 S.D. | (14.4–29.4) | (9.0–25.6) | (0.7–1.9) |
| Patients with pancreatic disease and steatorrhea | | | | | | | |
| 12 | 66 | F | 47 | adenocarcinoma pancreas, Whipple procedure, 100% pancreatectomy | 23.1 | 0.5 | 46.2 |
| 13 | 54 | M | 153 | chronic pancreatitis, idiopathic, pancreatic calcification | 23.6 | 0.6 | 39.3 |
| 14 | 46 | M | 39 | chronic pancreatitis, Etoh, 90% pancreatectomy | 18.4 | 0.9 | 20.4 |
| 15 | 18 | M | 51 | cystic fibrosis | 13.6 | 0.7 | 19.4 |
| 16 | 67 | M | 38 | chronic pancreatitis, Etoh, indurated pancreas as laporotomy | 18.1 | 1.1 | 17.0 |
| 17 | | M | 12 | chronic pancreatitis, Etoh, pancreatic calcification | 14.0 | 1.2 | 11.7 |
| 18 | 38 | M | 18 | chronic pancreatitis, Type IV hyperlipidemia | 11.6 | 1.0 | 11.6 |
| 19 | 52 | M | 27 | chronic pancreatitis, Etoh, pancreatic calcification | 17.3 | 1.6 | 10.8 |
| 20 | 58 | M | 27 | chronic pancreatitis, Etoh, pancreatic calcification | 9.8 | 0.9 | 10.7 |
| 21 | 26 | F | 19 | gun shot wound, Whipple procedure, 75% pancreatectomy | 15.1 | 2.2 | 6.9 |
| | | | | mean | (16.5) | (1.1) | (19.4) |
| | | | | range | (9.8–23.6) | (0.5–2.2) | (6.9–46.2) |
| Patients with pancreatic disease without steatorrhea | | | | | | | |
| 22 | 49 | M | 3 | chronic pancreatitis, Etoh, pancreatic calcification, 25% pancreatectomy, moderate fibrosis | 14.4 | 5.8 | 2.5 |
| 23 | 25 | M | 6 | acute pancreatitis, chronic steroid therapy for asthma | 30.5 | 20.9 | 1.5 |
| 24 | 36 | M | 2 | chronic pancreatitis, Etoh | 23.0 | 19.2 | 1.2 |
| | | | | mean | (22.6) | (15.3) | (1.7) |
| | | | | range | (14.4–30.5) | (5.8–20.9) | (1.2–2.5) |
| Patients with other gastrointestinal diseases | | | | | | | |
| 25 | 18 | F | 39 | Crohn's disease, mesenteric infarction, 95% sm. bowel resection | 1.1 | 0.5 | 2.2 |
| 26 | | F | 27 | Ca cervix, radiation enteritis, bacterial overgrowth | 3.9 | 1.9 | 2.1 |
| 27 | 60 | M | | sprue, pernicious anemia | 4.6 | 2.4 | 1.9 |
| 28 | 68 | M | | sprue | 0.9 | 0.5 | 1.8 |
| 29 | 52 | F | | sprue | 5.8 | 3.7 | 1.6 |
| 30 | | F | | mesenteric infarction, % sm. bowel resection | 0.3 | 0.2 | 1.5 |
| 31 | 47 | M | 8 | sprue | 13.3 | 9.5 | 1.4 |
| 32 | 27 | F | | pernicious anemia | 18.4 | 13.9 | 1.3 |
| 33 | 72 | F | 9 | scleroderma, giardiasis, bacterial overgrowth | 17.7 | 14.7 | 1.2 |
| 34 | 30 | M | | Crohn's disease, ileal resection | 0.7 | 0.6 | 1.2 |
| | | | | mean | (6.7) | (4.8) | (1.6) |
| | | | | range | (0.3–18.4) | (0.2–14.7) | (1.2–2.2) |
| Patients with pancreatic disease and other gastrointestinal diseases | | | | | | | |
| 35 | 57 | M | | chronic pancreatitis, pseudocyst, Crohn's disease, ileal resection | 2.3 | 0.4 | 5.8 |
| 36 | 45 | M | 19 | pseudocyst, Whipple procedure, 90% pancreatectomy, sprue | 4.3 | 0.2 | 21.5 |
| Patients with pancreatic disease and renal insufficiency | | | | | | | |
| 37 | 54 | F | 40 | chronic pancreatitis, Etoh, pancreatic calcification, renal insufficiency (creatinine clearance 6 ml/min) | 5.7 | 1.3 | 4.4 |
| 38 | 61 | F | | adenocarcinoma pancreas, whipple procedure, total pancreatectomy, renal insufficiency (creatinine clearance 20 ml/min) | 6.6 | 0.3 | 22.0 |

Orally administered solutions were the same as those used in TABLE 4 except that in 20 subjects 1, 5, 6, 10, 12, 16, 17, 23, 27, 32, 33 and 35 the radioactive forms of $B_{12}$ were reversed such that [$^{58}$Co]$B_{12}$** was given bound to IF and [$^{57}$Co]$B_{12}$* was given bound to hog R.
+Normal <7 g/day In 10 patients with pancreatic disease severe enough to cause steatorrhea (malabsorption of fat), as documented independently by tests for elevated fecal fat contents, values for $B_{12}^*$ originating as IF-$B_{12}^*$ were close to values of $B_{12}^*$ for normal subjects and ranged from about 9.8% to 23.3% (mean 16.5%). The reason for the slight reductions of $B_{12}^*$, originating as IF-$B_{12}^*$, seen in some patients is unknown although they could be due to incomplete urine collections, or minor abnormalities of intestinal pH, bacterial overgrowth, or intestinal mucosa integrity. However, for these same patients the values for $B_{12}$ originating as hog R protein-$B_{12}$ were uniformly and markedly reduced, ranging from about 0.5% to 2.2% (mean 1.2%). Values for the ratio of urine excreted $B_{12}^*$ to $B_{12}$ were markedly elevated and ranged from about 6.9 to 46.2 (mean 19.4). The values for $B_{12}$ and the ratio of $B_{12}^*$ to $B_{12}$ did not overlap with the values for any of the normal subjects. The degree of elevation of the ratio of $B_{12}^*$ to $B_{12}$ appeared to be in agreement with the severity of steatorrhea since the 5 patients with the highest ratios were the same 5 patients that also had the highest fecal fat contents. While correlation was not perfect, this may have been due to the fact that the patients were not on diets of defined fat content while feces were being collected for the fecal fat tests.

Using the test of the present invention, two other patients with pancreatic disease that did not cause steatorrhea had normal test reuslts while a third patient with a pancreatic disease had a slightly reduced value of 5.8% for $B_{12}^*$ and a slightly increased value of 2.5 for the ratio of $B_{12}^{**}$ to $B_{12}^*$. These results suggest that the tests of the present invention provide similar, and possibly somewhat superior results to the 72-hour fecal fat analysis in terms of its sensitivity in detecting patients with pancreatic exocrine insufficiency.

The specificity of the test of the present invention was assessed by performing it on 10 patients with a variety of gastrointestinal diseases that included Crohn's disease, sprue, small bowel resection, scleroderma, bacterial overgrowth, giardiasis and pernicious anemia. Vitamin $B_{12}$ malabsorption is frequently present in many of these diseases and values for $B_{12}^{}$ originating as IF-$B_{12}^{}$ ranged widely from about 0.3% to 18.4% (mean 6.7%) in these patients. Values for $B_{12}^*$ originating as R-$B_{12}^*$ were reduced proportionately, however, and ranged from about 0.2% to 14.7% (mean 4.8%). This resulted in values for the ratio $B_{12}^{**}$ to $B_{12}^*$ that ranged from about 1.2 to 2.2 (mean 1.6), which were very similar to the ratios of normal subjects. Values for the $B_{12}^{**}$ to $B_{12}^*$ ratio in these subjects with gastrointestinal disease did not overlap with those obtained for patients with pancreatic disease severe enough to cause steatorrhea.

It is of interest to note the fact that 4 patients within the intestinal disease group had documented steatorrhea. This demonstrates that steatorrhea itself is not responsible for elevated values for the ratios of $B_{12}^{**}$ to $B_{12}^*$.

One patient with both pancreatic disease and Crohn's disease, and a second patient with both pancreatic disease and sprue, were studied to determine if the test could detect pancreatic exocrine insufficiency in the face of superimposed intestinal disease. In the first patient, with Crohn's disease, the value for $B_{12}^{}$ originating as IF-$B_{12}^{}$ was reduced to 3.2%, but the value for $B_{12}^*$ originating as R-$B_{12}^*$ was reduced even further to 0.4% thus giving an elevated value of 5.8 for the ratio of $B_{12}^{**}$ to $B_{12}^*$. In the second patient, with sprue, the value for $B_{12}^{**}$ was reduced to 6.6% but the value for $B_{12}^*$ was reduced disproportionately to 0.3% thus giving an elevated value of 22.0 for the ratio of $B_{12}^{**}$ to $B_{12}^*$. These results indicate that the test of the present invention is capable of detecting pancreatic exocrine insufficiency even in the presence of superimposed intestinal disease.

Two patients with combined pancreatic and renal disease were studied, since it is known that the urinary excretion of $B_{12}$ is reduced in patients with renal disease. Both patients had low values for $B_{12}^{}$ originating as IF-$B_{12}^{}$, 5.7% and 6.6% respectively, but their values for $B_{12}^*$ originating as R-$B_{12}^*$ were reduced disproportionately to 1.3% and 0.3% respectively. Consequently, their values for the raatio of $B_{12}^{**}$ to $B_{12}^*$ of 4.4 and 22.0 respectively, were both elevated. These results indicate that the test of the present invention can detect pancreatic exocrine insufficiency in patients with superimposed renal disease provided that such patients are not anuric.

Using the equivalent of the present invention, plasma levels of absorbed $B_{12}$ can be monitored and are especially useful in patients who are anuric. Plasma levels could also be used in subjects without renal disease, as has been done with standard $B_{12}$ absorption tests, although here the injection of unlabelled $B_{12}$ would be omitted since such omission increases plasma levels of recently absorbed labelled $B_{12}$.

In most of the studies presented in Table 5, ($^{57}$Co) $B_{12}^{**}$ was given bound to intrinsic factor and ($^{58}$Co)$B_{12}^*$ was given bound to hog R protein. However, the labelling isotopes were reversed, in at least several subjects in each major group and this did not appear to influence the results of the test.

TABLE 6

Time course of urinary excretion of radioactivity after the simultaneous oral administration of Human intrinsic factor (IF)-($^{57}$Co)$B_{12}^{**}$ and Hog R protein-$C^{58}$Co)$B_{12}^*$ in pancreatic tests.#

| Subject | Time after oral administration (Hr) | Percentages of administered $B_{12}$ excreted in 24 hour urine | | |
|---|---|---|---|---|
| | | IF-$B_{12}^{**}$ (%) | R-$B_{12}^*$ (%) | IF-$B_{12}^{**}$/R-$B_{12}^*$ |
| Patient with | 0–8 | 8.52 | 0.45 | 18.9 |
| pancreatic | 8–16 | 5.02 | 0.27 | 18.6 |
| exocrine | 16–24 | 0.060 | 0.004 | 15.0 |
| insufficiency+ | 0–24 | 13.600 | 0.724 | 18.9 |
| Normal++ | 0–8 | 4.30 | 3.53 | 1.22 |
| | 8–16 | 10.59 | 9.30 | 1.14 |
| | 16–24 | 3.97 | 3.53 | 1.12 |
| | 0–24 | 18.86 | 16.36 | 1.15 |

Orally administered solution were the same as those used in TABLE 4.
+The patient was No. 15 per TABLE 5.
+30 Subject No. 8 per TABLE 5.

It has been determined that the time course of the urinary excretion of $B_{12}^{**}$ and $B_{12}^*$ is not critical. The time course of the urinary excretion of $B_{12}^{}$ originating as IF-$B_{12}^{}$ and $B_{12}^*$ originating as R-$B_{12}^*$ for one patient with pancreatic exocrine insufficiency and one normal subject are presented in Table 6. The data indicate that in both cases the ratio of $B_{12}^{**}$ to $B_{12}^*$ was highest in the 0 to 8 hour samples and lowest in the 16 to 24 hour samples. However, differences were slight, during these time periods, and this suggests that the additional time required for pancreatic enzymes to act on $B_{12}$ originating as hog R-$B_{12}$ and effect the transfer of such $B_{12}$ to IF is small compared with the time required for such $B_{12}$ to reach the ileum and be absorbed. Because the ratio differences at various times were small, the inadvertent loss of individual urine samples during a 24-hour collection would not be expected to have a major effect on the value obtained for the ratio. The data presented in Table 6 also indicate that one could utilize 0 to 8 hour urine collections to evaluate patients for pancreatic exocrine insufficiency if time was a critical factor.

The model upon which the present invention is based can also serve to explain certain anomalies noted in situations of $B_{12}$ absorption in certain cases of pancreatic exocrine dysfunction. Vitamin $B_{12}$ malabsorption in pancreatic creatic insufficiency has been corrected by the oral administration of bicarbonate, pancreatic proteases or the $B_{12}$ analogue cobinamide. The model on which the present invention is based provides an explanation for the action of each of these seemingly diverse $B_{12}$ mal-absorption correcting agents. Bicarbonate exerts its effect by neutralizing gastric acid since at neutral (non-acid) pH IF can partially compete with R protein for the initial binding and retention of $B_{12}$, thus providing IF-$B_{12}$ for absorption. Pancreatic proteases function by partially degrading R protein and lowering its affinity for $B_{12}$ by 150-fold, and these changes result in the rapid transfer of $B_{12}$ from R protein to IF, again providing IF-$B_{12}$ for absorption. Cobinamide $B_{12}$ analogue binds to R protein with high affinity, but does not bind to IF. This $B_{12}$ analogue functions by saturating endogenous R protein and leaving IF as the only binder available for binding $B_{12}$, thus again providing IF-$B_{12}$ for absorption.

The model on which the present invention is based also provides an explanation for the fact that many patients with severe pancreatic exocrine insufficiency have normal Schilling tests since achlorhydria has the same effect as oral bicarbonate and is frequently superimposed with this exocrine insufficiency, and also since some variation does exist in the R protein content of basal gastric juice.

The data presented herein provides support for the present $B_{12}$ absorption model and the test of the present invention. It shows that $B^{57}_{12}$ given orally bound to R protein was malabsorbed markedly by all 10 subjects studied with pancreatic exocrine insufficiency severe enough to cause steatorrhea. Simultaneously administered $B^{58}_{12}$ given bound to IF, and given with cobinamide $B_{12}$ analogue resulted in the $B^{58}_{12}$ being absorbed in essentially normal amounts, by all of these same subjects. This observation provides strong evidence against the concept that pancreatic proteases alter the structure of IF in a manner that is required for $B_{12}$ absorption. Preferential malabsorption of $B^{57}_{12}$ originating as R-$B^{57}_{12}$ was not observed at all in a variety of intestinal diseases. This indicates that the abnormalities in $B_{12}$ malabsorption frequently seen with intestinal diseases are not due to interference with the partial degradation of R protein by pancreatic proteases or with the transfer of $B^{57}_{12}$ to intrinsic factor, even though these steps do take place within the intestine.

The dual label test of the present invention is faster than the 72-hour fecal fat analysis and is more convenient and less disagreeable for the subject and laboratory personnel than either duodenal intubation tests or the fecal fat analysis. The present test also possesses the potential of being much more easily available than either of the two current tests for pancreatic exocrine function since it could be performed by any physician with access to a rudimentary nuclear medicine facility, provided that the test components were available.

The tests of the present invention are specific for pancreatic exocrine insufficiency. Such specificity is not possessed by the fecal fat analysis, since this test is also abnormal in a variety of intestinal diseases. Specificity is important clinically since weight loss, diarrhea, and abdominal pain are common symptoms in both pancreatic and intestinal diseases. Specificity is also important in evaluating patients with known intestinal disease for the presence of superimposed pancreatic exocrine insufficiency.

Although the ratio of $B^{58}_{12}$ originating as IF-$B^{58}_{12}$ to $B_{12}$ originating as hog R-$B^{57}_{12}$ is the parameter which provides the test of the present invention with its specificity for pancreatic exocrine insufficiency, it should be noted that useful information is also provided by the values obtained for $B^{58}_{12}$ itself since a marked reduction in $B_{12}$ was often observed in patients with intestinal disease. However, as marked reductions for $B^{58}_{12}$ were not always observed, a normal value for IF-$B^{58}_{12}$ does not rule out the presence of intestinal disease.

Although most of the studies presented here utilized human IF, hog R protein, cobinamide $B_{12}$ analogue, $(^{57}Co)B_{12}$, and $(^{58}Co)B_{12}$, it is well established by the studies presented here and elsewhere that similar results could be obtained by substitution of equivalent compositions for these components. For example, other species of IF, such as hog IF, rat IF, and others could be used in place of or in combination with human IF. Other R proteins or other materials which bind $B_{12}$ and make it unavailable for binding to IF in the digestive system, unless pancreatic enzymes are present, could be used with or in place of hog R protein. These include human R protein and dog R protein and any other material with these properties.

Several techniques, other than the use of $B_{12}$ analogues exist for preventing endogenous R protein from removing $B_{12}$ from IF in the digestive system. One method would employ $B_{12}$ analogues in place of or in combination with cobinamide $B_{12}$ analogue, which other $B_{12}$ analogues also possess the property of binding to human R protein with substantially the same affinity as $B_{12}$ while binding with low affinity to IF. $B_{12}$ (bde-OH) and (3,4,6-Me$_3$benzimidazole)$B_{12}$ are examples of some other $B_{12}$ analogues which possess these properties. Another method of preventing R protein from removing $B_{12}$ from IF in the digestive system would provide for the effective removal or neutralization of acid in the subject's stomach, since at neutral or slightly alkaline pH R protein is much less effective in removing $B_{12}$ from IF than it is at acid pH. The acid could be neutralized by the oral administration of bicarbonate or other antacids or by the oral or parenteral administration of agents, such as the drug cimetidine, which limit the secretion of acid into the gastric juices.

Many labelled forms of vitamin $B_{12}$ are available for use in the practice of the present invention, such as $(^{56}Co)$-$B_{12}$ or $(^{60}Co)$-$B_{12}$ which could be utilized in place of $(^{57}Co)$-$B_{12}$ and $(^{58}Co)$-$B_{12}$.

Although the studies presented here measure the absorption of various labelled forms of $B_{12}$ with the Schilling technique, it is well established that similar results could be obtained by using other methods of measuring the absorption of labelled $B_{12}$. Examples of such applicable techniques include measuring labelled $B_{12}$ in feces or blood or by measuring the total body content or hepatic content of radioactive $B_{12}$ with nuclear scanning.

Although the studies presented here utilize two different labelled forms of $B_{12}$ so that the absorption of $B_{12}$ originating in both IF-$B_{12}$ and R-$B_{12}$ could be measured simultaneously, it is apparent that similar results could be obtained by using one labelled form of $B_{12}$ and measuring the absorption of IF-$B_{12}$ and R-$B_{12}$ on separate occasions.

While preferred embodiments have set forth concentrations and amounts of various components utilized in certain studies, the useful and preferred amounts of those components are set forth below:

| Composition | Useful Range | Preferred Range |
| --- | --- | --- |
| IF-$B_{12}$ | 0.002–20.0 nmol | 0.05–2.0 nmol |
| R-$B_{12}$ | 0.002–20.0 nmol | 0.05–2.0 nmol |
| Free IF | 0.05–100.0 nmol | 0.2–1.0 nmol |
| $B_{12}$ analogues | 0.2–20,000 nmol | 20–500 nmol |

While the invention has been particularly shown and described with reference to preferred embodiments thereof, it will be understood by those skilled in the art that the foregoing and other modifications or changes in form and detail may be made therein without departing from the spirit and scope of the invention.

What is claimed is:

1. In the method of testing pancreatic exocrine function of a subject the steps of:
   placing in the subject's digestive system a complex of (first) labelled vitamin $B_{12}$ bound to intrinsic factor protein (IF) said complex being designated as IF-$B_{12}$; and
   also placing in the subject's digestive system a composition including (second) labelled vitamin $B_{12}$ bound to binding (means), substance, (wherein said binding means bind with said second labelled $B_{12}$, and) wherein said binding (means) substance substantially inhibits the binding of said (second) labelled $B_{12}$ bound to said binding substance by IF in said subject's digestive system until said composition is acted upon by exocrine pancreatic enzymes.

2. The method of claim 1 wherein said subject has endogenous R protein in his digestive system and said subject (is caused to ingest) also ingests R protein blocking (means) substance for rendering said endogenous R protein substantially incapable of removing (said first) labelled $B_{12}$ from said IF-$B_{12}$ complex.

3. The method of claim 1 wherein said subject (is caused to ingest) also ingests unbound intrisic factor protein.

4. The method of claim 1 wherein said IF is selected from the group consisting of human intrinsic factor, hog intrinsic factor and rat intrinsic factor.

5. The method of claim 4 wherein said IF is human intrinsic factor.

6. The method of claim 1 wherein the binding (means for said second labelled vitamin $B_{12}$) substance is an R protein and said bound composition is an R-$B_{12}$ complex, said complex being designated as R-$B_{12}$.

7. The method of claim 6 wherein said R protein is selected from the group consisting of human R protein, dog R protein, and hot R protein.

8. The method of claim 7 wherein said R protein is hog R protein.

9. The method of claim 2 wherein said R protein blocking substance is a $B_{12}$ analogue which reacts with and substantially binds R protein, but which does not bind substantially with IF protein.

10. The method of claim 9 wherein said $B_{12}$ analogue is selected from the group consisting of cobinamide, $B_{12}$(bde-OH) and (3,5,6-Me$_3$benzimidazole)$B_{12}$.

11. The method of claim 10 wherein said $B_{12}$ analogue is cobinamide.

12. The method of claim 2 wherein said R protein blocking substance removes acid from the subject's stomach.

13. The method of claim 12 wherein said (acid removing means) R protein blocking substance is selected from the group consisting of antacids and (means) substances that limit secretion of acid into the digestive system.

14. The method of claim 13 wherein the antacid is sodium bicarbonate.

15. The method of claim 13 wherein the substance for limiting acid secretion is cimetidine.

16. The method of claim 1 wherein the labelled $B_{12}$ are selected from the group consisting of ($^{56}$Co)$B_{12}$, ($^{57}$Co)$B_{12}$, ($^{58}$Co)$B_{12}$ and ($^{60}$Co)$B_{12}$.

17. The method of claim 1 including the additional step of injecting the subject with unlabelled $B_{12}$ in an amount sufficient to react with and bind substantially all $B_{12}$ binding substances present in the subject's blood and plasma.

18. The method of claim 17 wherein the subject's excreted urine is subsequently collected and measured to determine the amount of (first) labelled $B_{12}$ that was bound to intrinsic factor and the amount of (second) labelled $B_{12}$ that was bound to the binding substance which (were) was absorbed and subsequently excreted.

19. The method of claim 1 where said (first) labelled $B_{12}$ that was bound to intrinsic factor and said (second) labelled $B_{12}$ bound to binding substance are labelled differently from one another.

20. The method of claim 1 wherein the IF-$B_{12}$ complex is ingested in an amount in the range of about 0.002 to about 20.0 nmol.

21. The method of claim 1 wherein the IF-$B_{12}$ complex is ingested in an amount in the range of about 0.05 to about 2.0 nmol.

22. The method of claim 1 wherein the IF-$B_{12}$ complex is ingested in an amount of about 0.2 nmol.

23. The method of claim 6 wherein the R-$B_{12}$ complex is ingested in an amount in the range of about 0.002 to about 20.0 nmol.

24. The method of claim 6 wherein the R-$B_{12}$ complex is ingested in an amount in the range of about 0.05 to about 2.0 nmol.

25. The method of claim 6 wherein the R-$B_{12}$ complex is ingested in an amount of about 0.2 nmol.

26. The method of claim 9 wherein said $B_{12}$ analogue is ingested in an amount in the range of about 0.2 to about 20,000 nmol.

27. The method of claim 9 wherein said $B_{12}$ analogue is ingested in an amount in the range of about 20 to about 500 nmol.

28. The method of claim 9 wherein said $B_{12}$ analogue is ingested in an amount of about 200 nmol.

29. The method of claim 3 wherein the unbound intrinsic factor is ingested in an amount in the range of about 0.05 to about 100 nmol.

30. The method of claim 3 wherein the unbound intrinsic factor is ingested in an amount in the range of about 0.2 to about 1.0 nmol.

31. The method of claim 3 wherein the unbound intrinsic factor is ingested in an amount of about 0.4 nmol.

32. The method of testing pancreatic exocrine function of a subject including the steps of:
   causing the subject to ingest into his digestive system a complex of $B_{12}$-IF, wherein said $B_{12}$ is labelled and is selected from the group consisting of radioactive ($^{56}$Co)$B_{12}$, ($^{57}$Co)$B_{12}$, ($^{58}$Co)$B_{12}$ and ($^{60}$Co)$B_{12}$;
   causing the subject to ingest a composition including second labelled vitamin $B_{12}$ bound to hog R protein, wherein said second labelled $B_{12}$ is different from said first labelled $B_{12}$ and is selected from the group consisting of radioactive ($^{56}$Co)$B_{12}$, ($^{57}$Co)$B_{12}$, ($^{58}$Co)$B_{12}$, and ($^{60}$Co)$B_{12}$;
   causing the subject to ingest endogenous R protein blocking substance in the form of $B_{12}$ analogue;
   causing the subject to ingest unbound intrinsic factor;
   injecting said subject with $B_{12}$;
   subsequently collecting said subject's excreted urine; and then measuring said excreted uring to determine the amount of said first labelled radioactive $B_{12}$ and the amount of said second labelled radioactive $B_{12}$.

33. A composition for use in testing pancreatic exocrine function and containing, in combination;
   a complex of IF and labelled $B_{12}$;
   a complex of R protein and labelled $B_{12}$; and
   $B_{12}$ analogue capable of binding substantially with R protein but not capable of binding substantially with IF.

34. The composition of claim 33 including, in addition, unbound intrinsic factor.

35. The method of providing a complex of labelled $B_{12}$ and intrinsic factor including the steps of obtaining gastric juices containing both IF and R protein;
   adding R protein binding material to said juices in an amount sufficient to bind substantially all of said R protein, said R protein binding material binding substantially with R protein and not binding substantially with IF; and
   adding labelled $B_{12}$ to said mixture either at the time that the R binding material is added or after said R binding material is added.

36. The method of claim 35 wherein said R protein binding material is a $B_{12}$ analogue and wherein it is present in an amount in the range of about 1 to about 1,000,000 times the amount of R protein in the sample.

37. The method of claim 36 wherein said $B_{12}$ analogue is selected from the group consisting of cobinamide, $B_{12}$(bde-OH) and (3,4,6-Me$_3$benzimidazole)$B_{12}$.

38. The labelled $B_{12}$-IF produced by the process of claim 36.

39. The method of claim 1 including the additional step of measuring the amount of labelled $B_{12}$ in the subject's blood or plasma.

40. The method of claim 1 including the additional step of measuring the amount of labelled $B_{12}$ in the subject's excreted feces, and then determining the amount of labelled $B_{12}$ which has been absorbed as the difference between the amounts of labelled $B_{12}$ which was ingested and the amount of labelled $B_{12}$ which is excreted in the feces.

41. The method of claim 1 wherein the subject is allowed to excrete all unabsorbed labelled $B_{12}$, wherein said labelled $B_{12}$ is radioactive, and wherein the amount of radioactivity retained in the subject's body is measured as an indication of absorbed $B_{12}$.

42. The method of claim 1 wherein said labelled $B_{12}$ bound to IF is placed in the subject's digestive system on one occasion and the said labelled $B_{12}$ bound to binding substance is placed in the subject's digestive system on a separate occasion.

43. The method of claim 1 wherein said labelled $B_{12}$ bound to IF, and said labelled $B_{12}$ bound to binding substance are placed in the subject's digestive system at substantially the same time.

44. The method of claim 42 wherein said labelled $B_{12}$ bound to IF and said labelled $B_{12}$ bound to binding substance contain the same label.

45. The method of claim 42 wherein said labelled $B_{12}$ bound to IF and said labelled $B_{12}$ bound to binding substance contain different labels.

46. The method of claim 43 wherein said labelled $B_{12}$ bound to IF and said labelled $B_{12}$ bound to binding substance contain different labels.

* * * * *